United States Patent
Lee et al.

(10) Patent No.: US 8,111,389 B2
(45) Date of Patent: Feb. 7, 2012

(54) METHOD OF INSPECTING DEFECTS IN CIRCUIT PATTERN OF SUBSTRATE

(75) Inventors: Seung Seoup Lee, Gyunggi-do (KR); Tak Gyum Kim, Gyunggi-do (KR); Jin Won Park, Gyunggi-do (KR)

(73) Assignee: Samsung Electro-Mechanics Co., Ltd., Gyunggi-Do (KR)

( * ) Notice: Subject to any disclaimer, the term of this patent is extended or adjusted under 35 U.S.C. 154(b) by 0 days.

(21) Appl. No.: 12/717,688

(22) Filed: Mar. 4, 2010

(65) Prior Publication Data

US 2011/0116084 A1    May 19, 2011

(30) Foreign Application Priority Data

Nov. 16, 2009 (KR) .................. 10-2009-0110424

(51) Int. Cl.
*G01N 21/00* (2006.01)
(52) U.S. Cl. .............. 356/237.1; 174/260; 174/261; 324/73.1; 324/500; 356/237.6; 356/239.3
(58) Field of Classification Search .... 356/237.1–237.6, 356/239.3; 324/767, 73.1, 500, 127; 174/260–261
See application file for complete search history.

(56) References Cited

U.S. PATENT DOCUMENTS

| | | | | |
|---|---|---|---|---|
| 5,122,737 A | * | 6/1992 | Clauberg | 324/767 |
| 7,397,596 B2 | * | 7/2008 | Yacoubian | 359/290 |
| 7,557,912 B2 | * | 7/2009 | Fukazawa et al. | 356/237.2 |
| 7,669,321 B1 | * | 3/2010 | Levy et al. | 174/260 |

FOREIGN PATENT DOCUMENTS

KR  10-2000-002349 A  4/2000

OTHER PUBLICATIONS

Office Action from counterpart Korean Patent Application No. 10-2009-0110424, Apr. 25, 2011, 4 pages.

\* cited by examiner

*Primary Examiner* — Gregory J Toatley
*Assistant Examiner* — Iyabo S Alli
(74) *Attorney, Agent, or Firm* — Blakely Sokoloff Taylor & Zafman LLP

(57) ABSTRACT

Disclosed herein is a method of inspecting defects in a circuit pattern of a substrate. At least one laser beam radiation unit for radiating a laser beam onto an inspection target circuit pattern of a substrate in a non-contact manner is prepared. A probe beam radiation unit for radiating a probe beam onto a connection circuit pattern to be electrically connected to the inspection target circuit pattern in a non-contact manner is prepared. The laser beam is radiated onto the inspection target circuit pattern using the laser beam radiation unit. The probe beam is radiated onto the connection circuit pattern using the probe beam radiation unit, thus measuring information about whether the probe beam is diffracted, and a diffraction angle. Accordingly, the method can solve problems such as erroneous measurements caused by contact pressure and can reduce the time required for measurements.

4 Claims, 3 Drawing Sheets

METHOD OF INSPECTING DEFECTS IN CIRCUIT PATTERN OF SUBSTRATE

CROSS REFERENCE TO RELATED APPLICATION

This application claims the benefit of Korean Patent Application No. 10-2009-0110424, filed on Nov. 16, 2009, entitled "Inspection Method for Circuit Pattern of Substrate", which is hereby incorporated by reference in its entirety into this application.

BACKGROUND OF THE INVENTION

1. Technical Field

The present invention relates to a method of inspecting defects in the circuit pattern of a substrate.

2. Description of the Related Art

With the recent development of the electronics industry, the requirement that electronic parts be of high functionality has rapidly increased, and thus methods of inspecting the electrical characteristics of substrates when substrates are manufactured are also required to be of high precision, high speed and low cost. Meanwhile, although the requirements for high-speed measurement ensuring high reliability are strict, there is no efficient measurement method satisfying such requirements, and thus contact probe methods are currently being performed.

FIG. 1 is a sectional view showing a conventional apparatus for inspecting defects in a circuit pattern using contact pin probes. Hereinafter, a conventional apparatus and method for inspecting defects in a circuit pattern will be described with reference to FIG. 1.

The conventional apparatus for inspecting defects in a circuit pattern includes two pin probes 11 and 12, a voltage source 13 and an ammeter 14.

The first pin probe 11 is installed to come into contact with the inspection target circuit pattern 16 of a substrate 15, and inputs a voltage received from the voltage source 13 to the inspection target circuit pattern 16. Therefore, a conical portion of the first pin probe 11 is connected to the inspection target circuit pattern 16, and the portion of the first pin probe 11 which is opposite the conical portion is connected to the voltage source 13 through the lead wire of the first pin probe 11.

The second pin probe 12 is installed to come into contact with a connection circuit pattern 17, of which the electrical connection with the inspection target circuit pattern 16 is desired to be examined. Therefore, a conical portion of the second pin probe 12 is connected to the connection circuit pattern 17, and the portion of the second pin probe 12 which is opposite the conical portion is connected to the lead wire of the first pin probe 11.

The ammeter 14 is a component for measuring current flowing through a closed circuit, and is installed in series with lead wires connected to the first pin probe 11 and the second pin probe 12.

A conventional method of inspecting defects in a circuit pattern is described below.

When the inspection target circuit pattern 16 is normally connected to the connection circuit pattern 17, current flows from the voltage source 13 sequentially through the first pin probe 11, the inspection target circuit pattern 16, the connection circuit pattern 17, and the second pin probe 12. The current is measured by the ammeter 14, and the entire resistance can be measured by applying the current to the formula of Ohm's law, that is, $R=V/I$. Theoretically, when the inspection target circuit pattern 16 is normally connected to the connection circuit pattern 17, the resistance must be '0'. However, since there are resistances of the lead wires and the pin probes 11 and 12 themselves, the entire resistance is not '0' and is derived as a relatively small value.

In contrast, when the inspection target circuit pattern 16 is not normally connected to the connection circuit pattern 17, current does not flow through a closed circuit, and the resistance becomes infinite.

Accordingly, the above resistances are compared with each other, and thus whether defects are present in the circuit pattern can be examined.

However, as described above, in the case where the contact pin probes 11 and 12 are used both in the inspection target circuit pattern 16 and in the connection circuit pattern 17, even if the circuit patterns are not normally connected, the circuit patterns may be measured as if they were normally connected to each other due to the contact pressure of the pin probes 11 and 12. That is, there is a problem in that the occurrence of erroneous measurements may increase.

Further, there is a problem in that the pin probes 11 and 12 come into contact with all unit circuit patterns, thus increasing the time required for measurements.

SUMMARY OF THE INVENTION

Accordingly, the present invention has been made keeping in mind the above problems occurring in the prior art, and the present invention is intended to provide a method of inspecting defects in the circuit pattern of a substrate, wherein a laser beam is radiated onto an inspection target circuit pattern in a non-contact manner, and a probe beam is radiated onto a connection circuit pattern in a non-contact manner, thus reducing the occurrence of erroneous measurements.

Further, the present invention is intended to provide a method of inspecting defects in the circuit pattern of a substrate, wherein a laser beam is radiated onto an inspection target circuit pattern in a non-contact manner, and a probe beam is radiated onto a connection circuit pattern in a non-contact manner, thus reducing the time required for taking measurements.

In accordance with a first aspect of the present invention, there is provided a method of inspecting defects in a circuit pattern of a substrate, comprising (A) preparing at least one laser beam radiation unit for radiating a laser beam onto an inspection target circuit pattern of a substrate in a non-contact manner, (B) preparing a probe beam radiation unit for radiating a probe beam onto a connection circuit pattern to be electrically connected to the inspection target circuit pattern in a non-contact manner, (C) radiating the laser beam onto the inspection target circuit pattern using the laser beam radiation unit, and (D) radiating the probe beam onto the connection circuit pattern using the probe beam radiation unit, thus measuring information about whether the probe beam is diffracted, and a diffraction angle.

In this case, the method further comprises (E) determining, based on the information about whether the probe beam is diffracted and the diffraction angle, whether defects are present in the circuit pattern of the substrate.

Further, the laser beam is a laser beam for generating surface acoustic waves.

Further, the substrate is a printed circuit board or a semiconductor wafer.

Further, at (C), when the laser beam is radiated onto the inspection target circuit pattern, surface acoustic waves are generated on the inspection target circuit pattern and are transferred to an inner layer of the substrate.

Further, the laser beam radiated by the laser beam radiation unit is a femtosecond laser beam.

Further, the inspection target circuit pattern and the connection circuit pattern of the substrate are connected to each other through a via.

In accordance with a second aspect of the present invention, there is provided a method of inspecting defects in a circuit pattern of a substrate, wherein the laser beam radiation unit comprises a plurality of laser beam radiation units in the method in accordance with the first aspect of the present invention, thus radiating laser beams onto one location of the inspection target circuit pattern of the substrate so that the laser beams meet at the location.

DESCRIPTION OF THE PREFERRED EMBODIMENTS

Figure 1:
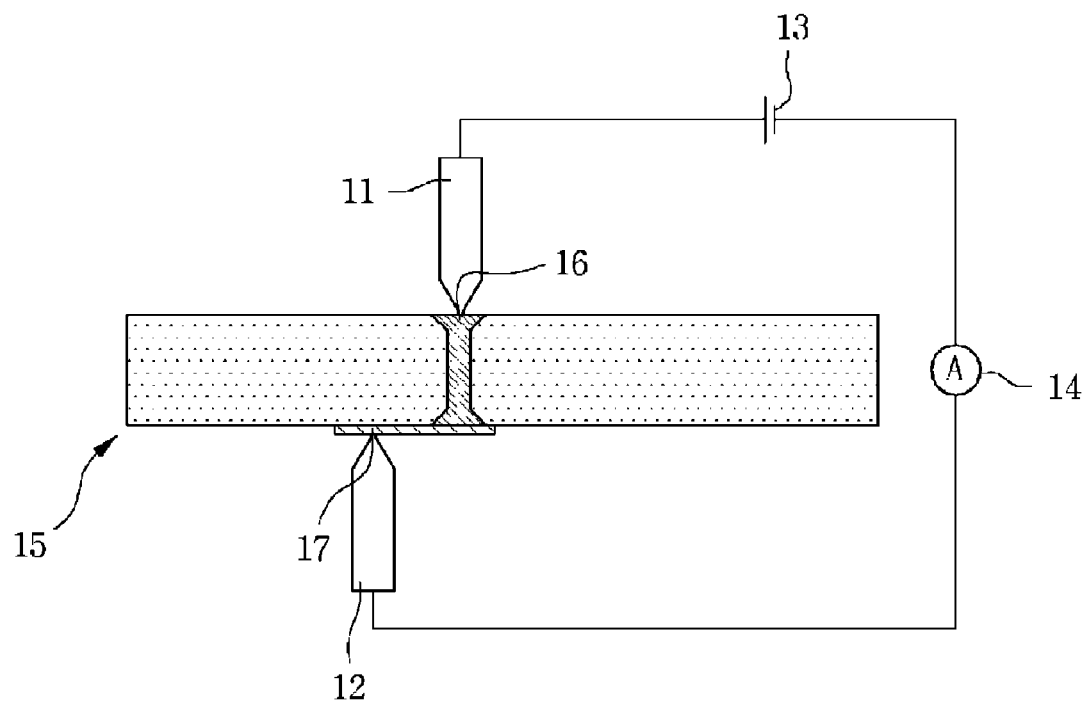
FIG. 1 is a sectional view showing a conventional apparatus for inspecting defects in a circuit pattern using pin probes.

Prior to giving the description, the terms and words used in the present specification and claims should not be interpreted as being limited to their typical meaning based on the dictionary definitions thereof, but should be interpreted to have the meaning and concept relevant to the technical spirit of the present invention, on the basis of the principle by which the inventor can suitably define the implications of terms in the way which best describes the invention.

The above and other objects, features and advantages of the present invention will be more clearly understood from the following detailed description taken in conjunction with the accompanying drawings. In the present specification, reference now should be made to the drawings, in which the same reference numerals are used throughout the different drawings to designate the same or similar components. Further, the above terms are used to distinguish one component from the other component, and the components of to the present invention are not limited by the terms. Further, in the description of the present invention, if detailed descriptions of related well-known constructions or functions are determined to make the gist of the present invention unclear, the detailed descriptions will be omitted.

Hereinafter, embodiments of the present invention will be described in detail with reference to the attached drawings.

Figure 2:
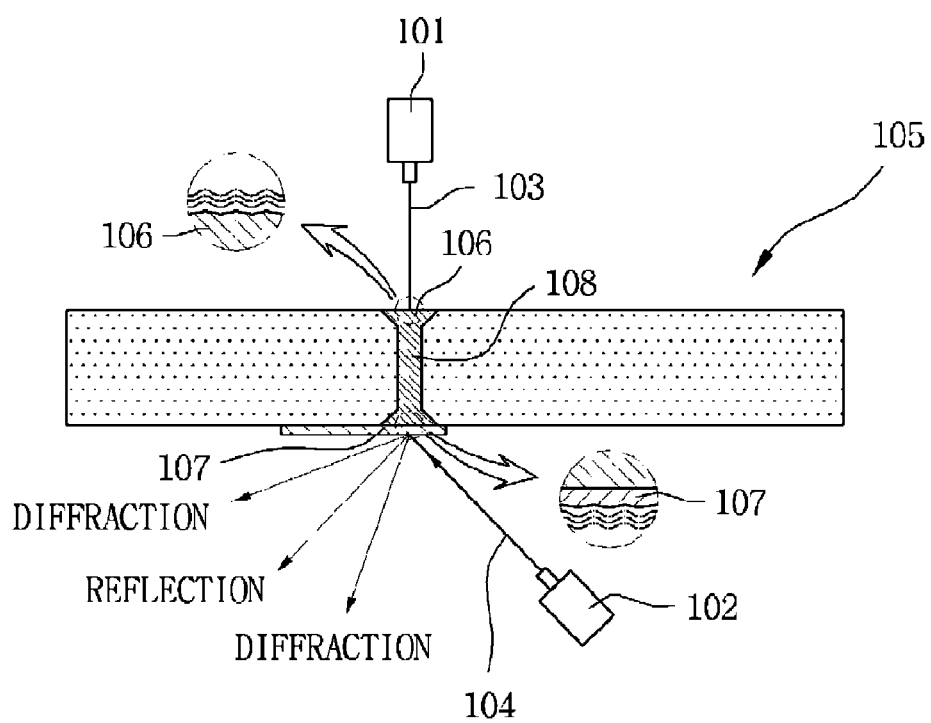
FIG. 2 is a view showing the state in which an inspection target circuit pattern is normally connected to a connection circuit pattern according to a first embodiment of the present invention.
Figure 3:
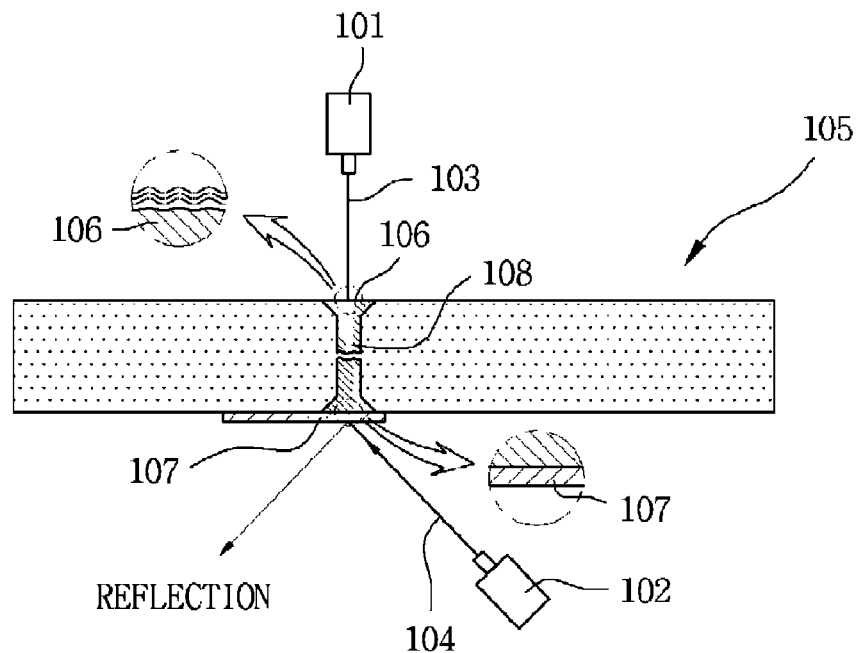
FIG. 3 is a view showing the state in which the inspection target circuit pattern is not connected to the connection circuit pattern according to a first embodiment of the present invention.

FIG. 2 is a view showing the state in which an inspection target circuit pattern 106 is normally connected to a connection circuit pattern 107 according to a first embodiment of the present invention. FIG. 3 is a view showing the state in which the inspection target circuit pattern 106 is not connected to the connection circuit pattern 107 according to a first embodiment of the present invention. Hereinafter, a method of inspecting defects in the circuit pattern of a substrate according to the present invention will be described with reference to the above drawings.

First, a laser beam radiation unit 101 for radiating a laser beam 103 onto the inspection target circuit pattern 106 of the substrate in a non-contact manner is prepared.

The laser beam 103 radiated by the laser beam radiation unit 101 may preferably be radiated by a high-power laser such as a femtosecond laser or an Nd:YAG laser. In this case, the femtosecond laser is a high-power laser having a pulse width of about more than several femtoseconds, and is capable of outputting instantaneous power in terawatts. The Nd:YAG laser is a high-power laser which is implemented using a flashlamp or a laser diode, outputs a power of 20 megawatts in Q-switch mode, and has a pulse width of 10 nanoseconds. The reason for using the high-power laser in this way is that a high-power laser is preferably used to generate surface acoustic waves on the inspection target circuit pattern 106 and measure the surface acoustic waves, which will be described later.

Next, a probe beam radiation unit 102 for radiating the probe beam 104 in a non-contact manner onto the connection circuit pattern 107, of which the electrical connection with the inspection target circuit pattern 106 is desired to be examined, is prepared.

In this case, the probe beam radiation unit 102 is installed in a direction diagonal to the connection circuit pattern 107 to enable a sufficiently large incidence angle, which will be described later, to be formed.

The probe beam 104 generated by the probe beam radiation unit 102 has a pulse width relatively greater than that of the laser beam 103 generated by the laser beam radiation unit 101. For example, the probe beam has a pulse width of about several hundreds of nanoseconds.

Meanwhile, since the laser beam radiation unit 101 and the probe beam radiation unit 102 are respectively installed with respect to the inspection target circuit pattern 106 and the connection circuit pattern 107 of the substrate 105 in a non-contact manner, as described above, erroneous measurements attributable to contact pressure do not occur.

Next, the laser beam 103 is radiated by the laser beam radiation unit 101 onto the inspection target circuit pattern 106.

In this case, when the high-power laser beam 103 is radiated onto the inspection target circuit pattern 106, surface acoustic waves are generated on the surface of the inspection target circuit pattern 106. These surface acoustic waves may be regarded as waves obtained when the optical energy of the laser beam 103 is converted into photoacoustic energy on the surface of the inspection target circuit pattern 106 while the laser beam 103 reaches the inspection target circuit pattern 106. Further, the optical energy of the laser beam 103 produces the standing waves of the surface acoustic waves on the excited inspection target circuit pattern 106. Such standing waves cause a kind of grating effect, thus resulting in a diffraction phenomenon and varying a refractive index. In this case, the high-power laser beam 103 can generate sufficient surface acoustic waves on the inspection target circuit pattern 106. Precise measurements can be performed using the probe beam 104 only when the intensity of the surface acoustic waves is sufficiently high.

Meanwhile, when the inspection target circuit pattern 106 is connected to the connection circuit pattern 107, the surface acoustic waves generated on the inspection target circuit pattern 106 are transferred up to the connection circuit pattern 107. In contrast, when the inspection target circuit pattern 106 is not connected to the connection circuit pattern 107, the surface acoustic waves are not transferred up to the connection circuit pattern 107. Further, even in the case where the inspection target circuit pattern 106 is not connected to the connection circuit pattern 107, surface acoustic waves can be transferred to the connection circuit pattern 107 after passing through an insulating layer. Even in that case, the number of surface acoustic waves is relatively insignificant compared to that of surface acoustic waves generated when the inspection target circuit pattern 106 is connected to the connection circuit pattern 107.

Next, the probe beam 104 generated by the probe beam radiation unit 102 is radiated onto the connection circuit pattern 107, so that information about whether the probe beam 104 is diffracted, and the angle of diffraction are measured.

The probe beam 104 is radiated onto the connection circuit pattern 107 to cause reflection or diffraction. The displacement and angle of diffraction of the probe beam are used to detect whether the inspection target circuit pattern 106 is connected to the connection circuit pattern 107.

In this case, as shown in FIG. 2, when the inspection target circuit pattern 106 is connected to the connection circuit pattern 107, surface acoustic waves are transferred up to the connection circuit pattern 107. Accordingly, the incident probe beam 104 is diffracted by the surface acoustic waves on the connection circuit pattern 107. That is, the incidence angle and the diffraction angle of the probe beam 104 may differ from each other. Further, even if diffraction occurs, part of the probe beam 104 may be reflected.

In contrast, as shown in FIG. 3, when the inspection target circuit pattern 106 is not connected to the connection circuit pattern 107, surface acoustic waves are not transferred to the connection circuit pattern 107. Accordingly, the incident probe beam 104 is reflected from the connection circuit pattern 107. That is, the incidence angle and the reflection angle of the probe beam 104 are identical to each other. Further, even if an insignificant number of surface acoustic waves generated on the inspection target circuit pattern 106 is transferred to the connection circuit pattern 107 through the insulating layer of the substrate 105, the intensity of the wave motion or the amplitude of the transferred surface acoustic waves is different from that obtained when the inspection target circuit pattern 106 is connected to the connection circuit pattern 107, thus resulting in a difference in the diffraction angle.

Meanwhile, the probe beam radiation unit 101 must be disposed at the location at which a sufficient incidence angle can be formed so that the probe beam 104 is reflected or diffracted.

Next, whether the probe beam 104 is diffracted is determined and whether defects are present in the circuit pattern is determined using the diffraction angle.

In this case, in the case where the probe beam 104 is radiated onto and diffracted from the fixed substrate 105, it is determined that the inspection target circuit pattern 106 is normally connected to the connection circuit pattern 107. Further, in the case where the probe beam 104 is not diffracted or where the diffraction angle is different from that obtained when the inspection target circuit pattern 106 is normally connected to the connection circuit pattern 107, it can be determined that the inspection target circuit pattern 106 is not connected to the connection circuit pattern 107.

Further, the reflected or diffracted probe beam 104 is measured by an optical detection unit (not shown) which is additionally installed. Measured information is input to a computer (not shown), so that the determination of whether the inspection target circuit pattern 106 is connected to the connection circuit pattern 107 may be derived.

The substrate 105 is an object to be inspected in the method of inspecting defects in the circuit pattern of a substrate according to the present embodiment, and is composed of an insulating layer and circuit patterns. Such a substrate 105 may include a printed circuit board or a semiconductor wafer.

Meanwhile, when the inspection target circuit pattern 106 and the connection circuit pattern 107 of the substrate 105 are connected to each other through a via 108, it is more preferable to use the method of inspecting defects in the circuit pattern of a substrate according to the present embodiment. The reason for this is that, in general, when the via 108 is formed, erroneous measurements caused by the contact pressure of the pin probe more frequently occur. Therefore, when the method of inspecting defects in the circuit pattern of a substrate according to the present invention is used, the laser beam radiation unit 101 is used on the top of the substrate in a non-contact manner, and the probe beam radiation unit 102 is used on the bottom of the substrate in a non-contact manner, thus solving the problems of conventional contact methods, such as the concealment of the separation of electrodes or erroneous measurements.

Figure 4:
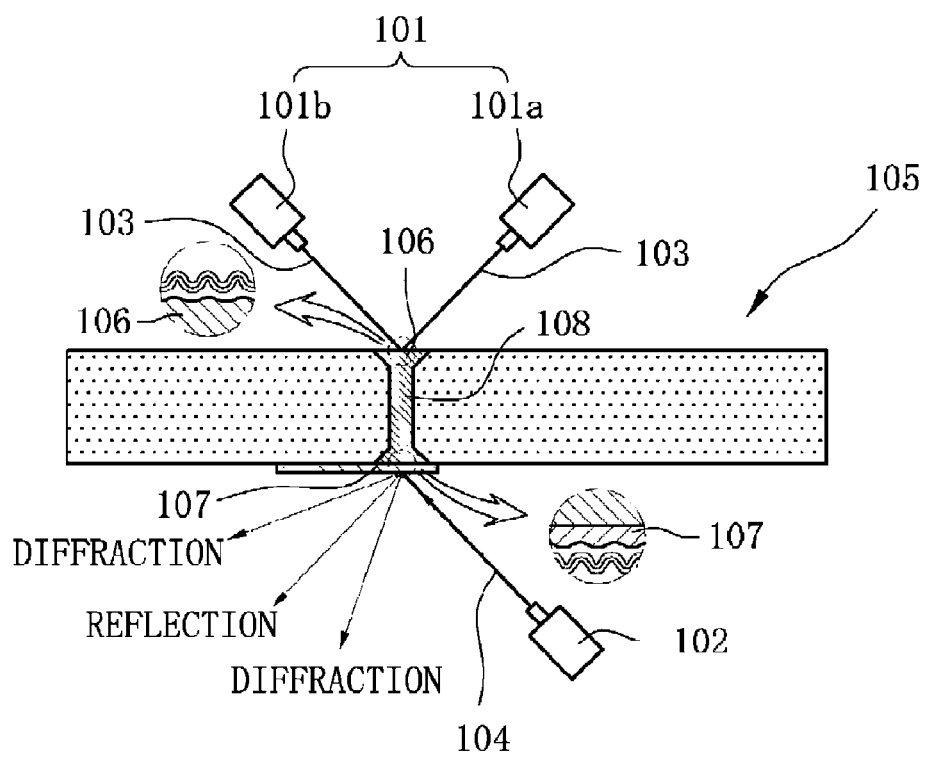
FIG. 4 is a view showing the state in which the inspection target circuit pattern is normally connected to the connection circuit pattern according to a second embodiment of the present invention.
Figure 5:
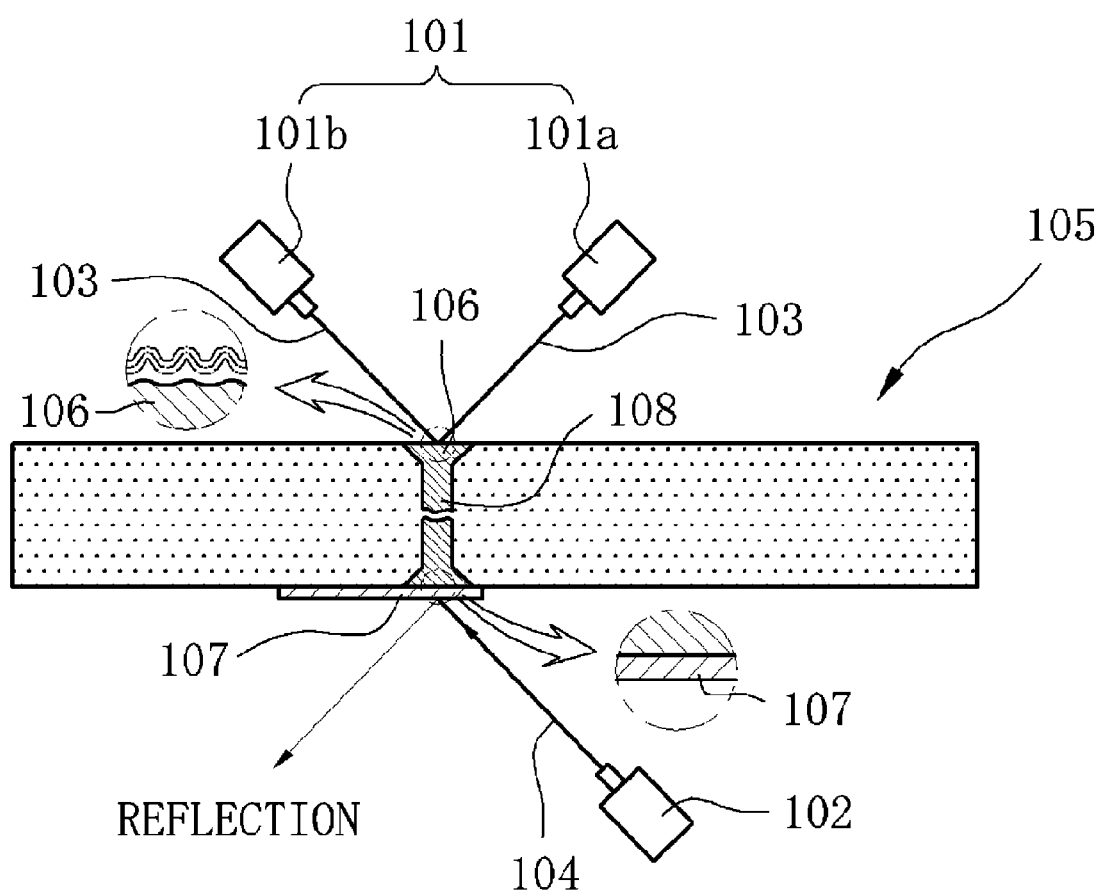
FIG. 5 is a view showing the state in which the inspection target circuit pattern is not connected to the connection circuit pattern according to a second embodiment of the present invention.

FIG. 4 is a view showing the state in which the inspection target circuit pattern 106 is normally connected to the connection circuit pattern 107 according to a second embodiment of the present invention. FIG. 5 is a view showing the state in which the inspection target circuit pattern 106 is not connected to the connection circuit pattern 107 according to a second embodiment of the present invention. Hereinafter, the method of inspecting defects in the circuit pattern of a substrate according to the present invention will be described with reference to the drawings. In this case, the same reference numerals are used to designate components identical or similar to those of the first embodiment. A repetitive description identical to that of the first embodiment will be omitted.

In the present embodiment, a plurality of laser beam radiation units 101 is provided, and laser beams 103 respectively radiated by the laser beam radiation units 101 are radiated onto one location of the inspection target circuit pattern 106 so that the laser beams 103 meet at the location. Surface acoustic waves can be generated on the inspection target circuit pattern 106 using a single high-power laser beam 103. However, when laser beams 103 are radiated by the plurality of laser beam radiation units 101, very high power can be obtained. Therefore, the intensity of the surface acoustic waves generated on the inspection target circuit pattern 106 can increase, and, as a result, the intensity of the surface acoustic waves transferred to the connection circuit pattern 107 can also increase. Therefore, when defects in the circuit pattern of the substrate are inspected, more precise measurements can be performed. Further, since equipment for the laser beam radiation units 101 is expensive, it is preferable to obtain high-power laser beams 103 using two laser beam radiation units 101.

As described above, a method of inspecting defects in the circuit pattern of a substrate according to the present invention provides is advantageous in that it measures whether defects are present in the circuit pattern by radiating a laser beam onto an inspection target circuit pattern in a non-contact manner using a laser beam radiation unit, and radiating a probe beam onto a connection circuit pattern in a non-contact manner using a probe beam radiation unit. Therefore, the present invention is advantageous in that the occurrence of erroneous measurements caused by the contact pressure of a pin probe (the concealment of the separation of electrodes) can be eliminated.

Further, the present invention is advantageous in that it measures whether defects are present in the circuit pattern by radiating a laser beam onto an inspection target circuit pattern in a non-contact manner, and radiating a probe beam onto a connection circuit pattern in a non-contact manner, thus reducing the time required for measurements because there is no need to bring a pin probe into contact with unit connection circuit patterns.

Furthermore, the present invention is advantageous because a pin probe is not used, thus reducing costs incurred by the consumption of parts.

Furthermore, the present invention is advantageous in that a plurality of laser beams is radiated to meet, thus obtaining high-power laser beams.

In addition, the present invention is advantageous in that, when repetitive inspections are performed, all circuit patterns are inspected under the same conditions, thereby improving repeatability/reproducibility and measurement reliability.

Although the preferred embodiments of the present invention have been disclosed for illustrative purposes, those skilled in the art will appreciate that the above embodiments are intended to describe the present invention in detail and the method of inspecting defects in the circuit pattern of a substrate according to the present invention is not limited thereto and that various modifications, additions and substitutions are possible, without departing from the scope and spirit of the invention as disclosed in the accompanying claims.

Simple modifications or changes of the present invention belong to the scope of the present invention, and the detailed scope of the present invention will be more clearly understood by the accompanying claims.

What is claimed is:

1. A method of inspecting defects in a circuit pattern of a substrate in a non contact manner, comprising:
   preparing at least one laser beam radiation unit for radiating a laser beam onto an inspection target circuit pattern of a substrate in a non-contact manner;
   preparing a probe beam radiation unit for radiating a probe beam onto a connection circuit pattern, wherein, the connection circuit pattern is supposed to be electrically connected to the inspection target circuit pattern through a via that passes through an inner layer of the substrate between the inspect target circuit pattern and the connection circuit pattern;
   radiating the laser beam onto the inspection target circuit pattern using the laser beam radiation unit, the radiating of the laser beam causing first surface acoustic waves to be generated on the inspection target circuit pattern's surface, and, if the via connects the inspection target circuit pattern to the connection circuit pattern, acoustic energy propagates through the via to generate second surface acoustic waves on the connection circuit pattern's surface; and
   radiating the probe beam onto the connection circuit pattern using the probe beam radiation unit, and, if the via connects the inspection target circuit pattern to the connection circuit pattern, then, the second surface acoustic waves on the connection circuit pattern's surface causes detectable variation of a diffraction angle of the probe beam, and, to determine in a non contact manner whether the via connects the inspection target circuit pattern to the connection circuit pattern, measuring information about whether the probe beam is diffracted, and a diffraction angle of the probe beam.

2. The method as set forth in claim 1, wherein the substrate is a printed circuit board or a semiconductor wafer.

3. The method as set forth in claim 1, wherein the laser beam radiation unit comprises a plurality of laser beam radiation units, thus radiating laser beams onto one location of the inspection target circuit pattern of the substrate so that the laser beams meet at the location.

4. The method as set forth in claim 1, wherein the laser beam radiated by the laser beam radiation unit is a femtosecond laser beam.

* * * * *